US009869511B2

(12) United States Patent
Valencia et al.

(10) Patent No.: US 9,869,511 B2
(45) Date of Patent: Jan. 16, 2018

(54) METHOD AND DEVICE FOR SEPARATING HYDROCARBONS AND CONTAMINANTS WITH A SPRAY ASSEMBLY

(71) Applicants: Jaime A. Valencia, Houston, TX (US); David W. Maher, Houston, TX (US)

(72) Inventors: Jaime A. Valencia, Houston, TX (US); David W. Maher, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 540 days.

(21) Appl. No.: 14/516,683

(22) Filed: Oct. 17, 2014

(65) Prior Publication Data
US 2015/0159943 A1 Jun. 11, 2015

Related U.S. Application Data

(60) Provisional application No. 61/912,957, filed on Dec. 6, 2013, provisional application No. 62/044,770, filed on Sep. 2, 2014.

(51) Int. Cl.
*F25J 3/00* (2006.01)
*F25J 1/00* (2006.01)
(Continued)

(52) U.S. Cl.
CPC ............. *F25J 3/0266* (2013.01); *B01D 1/20* (2013.01); *B01D 3/32* (2013.01); *C07C 7/05* (2013.01);
(Continued)

(58) Field of Classification Search
CPC ........ F25J 3/0209; F25J 3/0233; F25J 3/0266; F25J 2280/40; F25J 2205/20; Y02C 10/12;
(Continued)

(56) References Cited

U.S. PATENT DOCUMENTS 2,621,216 A 12/1952 White ........................ 260/683.3
2,843,219 A 7/1958 Habgood ................... 183/114.2
(Continued)

FOREIGN PATENT DOCUMENTS

DE 3149847 11/1961 ............... B01D 5/00
EP 0133208 2/1985 ............. B01D 53/14
(Continued)

OTHER PUBLICATIONS

U.S. Appl. No. 14/516,686, filed Oct. 17, 2014, Valencia, J. A.
(Continued)

*Primary Examiner* — Keith Raymond
(74) *Attorney, Agent, or Firm* — ExxonMobil Upstream Research Company—Law Department

(57) ABSTRACT

A method for separating a feed stream in a distillation tower comprising maintaining a controlled freeze zone (CFZ) section in the distillation tower, receiving a freezing zone liquid stream in a spray nozzle assembly in the CFZ section, wherein the spray nozzle assembly comprises a plurality of outer spray nozzles on an outer periphery of the spray nozzle assembly and at least one inner spray nozzle interior to the outer spray nozzles, wherein each outer spray nozzle is configured to spray the freezing zone liquid stream along a central spray axis, and wherein the central spray axis of at least one of the outer spray nozzles is not parallel to a CFZ wall, and spraying the freezing zone liquid stream through the spray nozzle assembly into the CFZ section to keep a temperature and pressure at which the solid and the hydrocarbon-enriched vapor stream form.

7 Claims, 6 Drawing Sheets

(51) Int. Cl.
  *F25J 3/02* (2006.01)
  *F25J 3/06* (2006.01)
  *B01D 3/32* (2006.01)
  *C07C 7/05* (2006.01)
  *F25J 3/08* (2006.01)
  *B01D 1/20* (2006.01)
  *C10L 3/10* (2006.01)

(52) U.S. Cl.
  CPC ........... *F25J 1/0022* (2013.01); *F25J 3/0209* (2013.01); *F25J 3/0233* (2013.01); *F25J 3/061* (2013.01); *F25J 3/067* (2013.01); *F25J 3/0635* (2013.01); *F25J 3/08* (2013.01); *C10L 3/104* (2013.01); *C10L 2290/141* (2013.01); *C10L 2290/18* (2013.01); *C10L 2290/543* (2013.01); *C10L 2290/58* (2013.01); *F25J 2200/02* (2013.01); *F25J 2200/30* (2013.01); *F25J 2200/50* (2013.01); *F25J 2200/74* (2013.01); *F25J 2200/90* (2013.01); *F25J 2205/04* (2013.01); *F25J 2205/20* (2013.01); *F25J 2220/66* (2013.01); *F25J 2235/60* (2013.01); *F25J 2280/40* (2013.01); *F25J 2290/12* (2013.01); *F25J 2290/40* (2013.01); *Y02C 10/12* (2013.01)

(58) Field of Classification Search
  CPC .. C10L 3/104; C10L 2290/18; C10L 2290/36; C10L 2290/60; C10L 3/102; C10L 2200/02; C10L 2200/50; C10L 2200/74; C10L 2200/66; C10L 2200/90; C10L 2210/04; C10L 2220/66; C10L 2280/02; C10L 2280/40; C10L 2290/40; C10L 1/0027; C10L 3/0233; C10L 3/0266; C10L 3/067; C10L 3/0635; C10L 3/061
  USPC .................................................. 62/602, 929
  See application file for complete search history.

(56) References Cited

U.S. PATENT DOCUMENTS

| | | | |
|---|---|---|---|
| 2,863,527 A | 12/1958 | Herbert et al. | 183/115 |
| 2,960,837 A | 11/1960 | Swenson et al. | 62/24 |
| 3,050,950 A | 8/1962 | Karwat et al. | 62/13 |
| 3,109,726 A | 11/1963 | Karwat | 62/13 |
| 3,349,571 A | 10/1967 | Nebgen | 62/23 |
| 3,393,527 A | 7/1968 | Swensen et al. | 62/16 |
| 3,400,512 A | 9/1968 | McKay | 55/69 |
| 3,421,984 A | 1/1969 | Jensen et al. | 203/41 |
| 3,683,634 A | 8/1972 | Streich | 62/29 |
| 3,705,625 A | 12/1972 | Whitten et al. | 166/252 |
| 3,767,766 A | 10/1973 | Tjoa et al. | 423/220 |
| 3,824,080 A | 7/1974 | Smith et al. | 23/288 |
| 3,842,615 A | 10/1974 | Reigel et al. | 62/171 |
| 3,848,427 A | 11/1974 | Loofbourow | 62/260 |
| 3,895,101 A | 7/1975 | Tsuruta | 423/574 |
| 3,929,635 A | 12/1975 | Buriks et al. | 210/54 |
| 3,933,001 A | 1/1976 | Muska | 62/47 |
| 4,129,626 A | 12/1978 | Mellbom | 261/114 |
| 4,246,015 A | 1/1981 | Styring | 62/12 |
| 4,270,937 A | 6/1981 | Adler | 62/17 |
| 4,280,559 A | 7/1981 | Best | 166/302 |
| 4,281,518 A | 8/1981 | Muller et al. | 62/12 |
| 4,318,723 A | 3/1982 | Holmes et al. | 62/20 |
| 4,319,964 A | 3/1982 | Katz et al. | 202/172 |
| 4,336,233 A | 6/1982 | Appl et al. | 423/228 |
| 4,344,485 A | 8/1982 | Butler | 166/271 |
| 4,370,156 A | 1/1983 | Goddin et al. | 62/17 |
| 4,382,912 A | 5/1983 | Madgavkar et al. | 423/224 |
| 4,383,841 A | 5/1983 | Ryan et al. | 62/17 |
| 4,405,585 A | 9/1983 | Sartori et al. | 423/228 |
| 4,417,449 A | 11/1983 | Hegarty et al. | 62/28 |
| 4,417,909 A | 11/1983 | Weltmer | 62/12 |
| 4,421,535 A | 12/1983 | Mehra | 62/17 |
| 4,441,900 A | 4/1984 | Swallow | 62/29 |
| 4,459,142 A | 7/1984 | Goddin | 62/17 |
| 4,462,814 A | 7/1984 | Holmes et al. | 62/17 |
| 4,466,946 A | 8/1984 | Goddin et al. | 423/228 |
| 4,511,382 A | 4/1985 | Valencia et al. | 62/20 |
| 4,512,782 A | 4/1985 | Bauer et al. | 55/48 |
| 4,533,372 A | 8/1985 | Valencia et al. | 62/12 |
| 4,551,158 A | 11/1985 | Wagner et al. | 55/46 |
| 4,563,202 A | 1/1986 | Yao et al. | 62/17 |
| 4,592,766 A | 6/1986 | Kumman et al. | 62/18 |
| 4,602,477 A | 7/1986 | Lucadamo | 62/24 |
| 4,609,388 A | 9/1986 | Adler et al. | 62/12 |
| 4,636,334 A | 1/1987 | Skinner et al. | 252/377 |
| 4,695,672 A | 9/1987 | Bunting | 585/867 |
| 4,697,642 A | 10/1987 | Vogel | 166/263 |
| 4,710,213 A | 12/1987 | Sapper et al. | 62/28 |
| 4,717,408 A | 1/1988 | Hopewell | 62/20 |
| 4,720,294 A | 1/1988 | Lucadamo et al. | 62/31 |
| 4,747,858 A | 5/1988 | Gottier | 62/17 |
| 4,761,167 A | 8/1988 | Nicholas et al. | 62/17 |
| 4,762,543 A | 8/1988 | Pantermuehl et al. | 62/28 |
| 4,769,054 A | 9/1988 | Steigman | 62/12 |
| 4,822,393 A | 4/1989 | Markbreiter et al. | 62/17 |
| 4,831,206 A | 5/1989 | Zarchy | 585/737 |
| 4,923,493 A | 5/1990 | Valencia et al. | 62/13 |
| 4,927,498 A | 5/1990 | Rushmere | 162/168.3 |
| 4,935,043 A | 6/1990 | Blanc et al. | 62/20 |
| 4,954,220 A | 9/1990 | Rushmere | 162/168.3 |
| 4,972,676 A | 11/1990 | Sakai | 62/18 |
| 4,976,849 A | 12/1990 | Soldati | 208/351 |
| 5,011,521 A | 4/1991 | Gottier | 62/11 |
| 5,062,270 A | 11/1991 | Haut et al. | 62/12 |
| 5,120,338 A | 6/1992 | Potts et al. | 62/12 |
| 5,137,550 A | 8/1992 | Hegarty et al. | 55/43 |
| 5,152,927 A | 10/1992 | Rivers | 252/344 |
| 5,233,837 A | 8/1993 | Callahan | 62/38 |
| 5,240,472 A | 8/1993 | Sircar | 95/52 |
| 5,247,087 A | 9/1993 | Rivers | 544/357 |
| 5,265,428 A | 11/1993 | Valencia et al. | 62/36 |
| 5,335,504 A | 8/1994 | Durr et al. | 62/20 |
| 5,345,771 A | 9/1994 | Dinsmore | 62/18 |
| 5,567,396 A | 10/1996 | Perry et al. | 422/190 |
| 5,620,144 A * | 4/1997 | Strock | B01D 53/504 239/557 |
| 5,643,460 A | 7/1997 | Marble et al. | 210/705 |
| 5,700,311 A | 12/1997 | Spencer | 95/236 |
| 5,720,929 A | 2/1998 | Minkkinen et al. | 422/190 |
| 5,819,555 A | 10/1998 | Engdahl | 62/637 |
| 5,820,837 A | 10/1998 | Marjanovich et al. | 423/220 |
| 5,899,274 A | 5/1999 | Frauenfeld et al. | 166/401 |
| 5,956,971 A | 9/1999 | Cole et al. | 62/623 |
| 5,964,985 A | 10/1999 | Wootten | 201/40 |
| 5,983,663 A | 11/1999 | Sterner | 62/620 |
| 6,053,007 A | 4/2000 | Victory et al. | 62/619 |
| 6,053,484 A | 4/2000 | Fan et al. | 261/114.1 |
| 6,082,133 A | 7/2000 | Barclay et al. | 62/619 |
| 6,082,373 A | 7/2000 | Sakurai et al. | 134/1 |
| 6,162,262 A | 12/2000 | Minkkinen et al. | 23/295 |
| 6,223,557 B1 | 5/2001 | Cole | 62/613 |
| 6,240,744 B1 | 6/2001 | Agrawal et al. | 62/643 |
| 6,267,358 B1 | 7/2001 | Gohara et al. | 261/110 |
| 6,270,557 B1 | 8/2001 | Millet et al. | 95/96 |
| 6,274,112 B1 | 8/2001 | Moffett et al. | 423/338 |
| 6,294,056 B1 * | 9/2001 | Matsumoto | B01D 3/008 202/158 |
| 6,336,334 B1 | 1/2002 | Minkkinen et al. | 62/123 |
| 6,374,634 B2 | 4/2002 | Gallarda et al. | 62/620 |
| 6,401,486 B1 | 6/2002 | Lee et al. | 62/630 |
| 6,416,729 B1 | 7/2002 | DeBerry et al. | 423/573.1 |
| 6,442,969 B1 | 9/2002 | Rojey et al. | 62/618 |
| 6,500,982 B1 | 12/2002 | Hale et al. | 562/600 |
| 6,505,683 B2 | 1/2003 | Minkkinen et al. | 166/266 |
| 6,516,631 B1 | 2/2003 | Trebble | 62/630 |
| 6,517,801 B2 | 2/2003 | Watson et al. | 423/574.1 |
| 6,539,747 B2 | 4/2003 | Minta et al. | 62/620 |
| 6,560,990 B2 * | 5/2003 | Hayashida | B01D 3/20 261/103 |

(56) References Cited

U.S. PATENT DOCUMENTS

| | | | |
|---|---|---|---|
| 6,565,629 B1 | 5/2003 | Hayashida et al. | 95/211 |
| 6,605,138 B2 | 8/2003 | Frondorf | 95/160 |
| 6,631,626 B1 | 10/2003 | Hahn | 62/612 |
| 6,632,266 B2 | 10/2003 | Thomas et al. | 95/49 |
| 6,662,872 B2 | 12/2003 | Gutek et al. | 166/272.4 |
| 6,694,989 B2 | 2/2004 | Tsujimoto | |
| 6,708,759 B2 | 3/2004 | Leaute et al. | 166/272.4 |
| 6,711,914 B2 | 3/2004 | Lecomte | 62/625 |
| 6,735,979 B2 | 5/2004 | Lecomte et al. | 62/611 |
| 6,755,251 B2 | 6/2004 | Thomas et al. | 166/265 |
| 6,755,965 B2 | 6/2004 | Pironti et al. | 208/347 |
| 6,818,194 B2 | 11/2004 | Deberry et al. | 423/228 |
| 6,883,327 B1 | 4/2005 | Iijima et al. | 60/649 |
| 6,946,017 B2 | 9/2005 | Leppin et al. | 95/139 |
| 6,958,111 B2 | 10/2005 | Rust et al. | 202/158 |
| 6,962,061 B2 | 11/2005 | Wilding et al. | 62/613 |
| 7,001,490 B2 | 2/2006 | Wostbrock et al. | 203/1 |
| 7,004,985 B2 | 2/2006 | Wallace et al. | 48/198.3 |
| 7,066,986 B2 | 6/2006 | Haben et al. | 95/99 |
| 7,073,348 B2 | 7/2006 | Clodic et al. | 62/532 |
| 7,121,115 B2 | 10/2006 | Lemaire et al. | 62/625 |
| 7,128,150 B2 | 10/2006 | Thomas et al. | 166/266 |
| 7,128,276 B2 | 10/2006 | Nilsen et al. | 236/124 |
| 7,152,431 B2 | 12/2006 | Amin et al. | 62/637 |
| 7,211,128 B2 | 5/2007 | Thomas et al. | 95/135 |
| 7,211,701 B2 | 5/2007 | Muller et al. | 568/853 |
| 7,219,512 B1 | 5/2007 | Wilding et al. | 62/617 |
| 7,285,225 B2 | 10/2007 | Copeland et al. | 210/785 |
| 7,325,415 B2 | 2/2008 | Amin et al. | 62/541 |
| 7,424,808 B2 | 9/2008 | Mak | 62/625 |
| 7,437,889 B2 | 10/2008 | Roberts et al. | 62/619 |
| 7,442,231 B2 | 10/2008 | Landrum | 95/45 |
| 7,442,233 B2 | 10/2008 | Mitariten | 95/123 |
| 7,493,779 B2 | 2/2009 | Amin | 62/617 |
| 7,536,873 B2 | 5/2009 | Nohlen | 62/644 |
| 7,550,064 B2 | 6/2009 | Bassler et al. | 203/2 |
| 7,575,624 B2 | 8/2009 | Cartwright et al. | 95/51 |
| 7,597,746 B2 | 10/2009 | Mak et al. | 95/169 |
| 7,635,408 B2 | 12/2009 | Mak et al. | 95/187 |
| 7,637,984 B2 | 12/2009 | Adamopoulos | 95/45 |
| 7,637,987 B2 | 12/2009 | Mak | 95/160 |
| 7,641,717 B2 | 1/2010 | Gal | 95/187 |
| 7,662,215 B2 | 2/2010 | Sparling et al. | 95/172 |
| 7,691,239 B2 | 4/2010 | Kister et al. | 203/2 |
| 7,722,289 B2 | 5/2010 | Leone et al. | 405/53 |
| 7,729,976 B2 | 6/2010 | Hill et al. | 705/37 |
| 7,770,872 B2 | 8/2010 | Delatour | 261/110 |
| 7,795,483 B2 | 9/2010 | Kulprathipanja et al. | 585/24 |
| 7,806,965 B2 | 10/2010 | Stinson | 95/187 |
| 7,814,975 B2 | 10/2010 | Hagen et al. | 166/257 |
| 7,879,135 B2 | 2/2011 | Ravikumar | 95/11 |
| 7,901,583 B2 | 3/2011 | McColl et al. | 210/710 |
| 7,955,496 B2 | 6/2011 | Iqbal et al. | 208/129 |
| 8,002,498 B2 | 8/2011 | Leone et al. | 405/53 |
| 8,020,408 B2 | 9/2011 | Howard et al. | 62/646 |
| 8,133,764 B2 | 3/2012 | Dirks et al. | 438/124 |
| 8,136,799 B2 | 3/2012 | Griepsma | 261/114.5 |
| 8,303,685 B2 | 11/2012 | Schubert et al. | 95/181 |
| 8,308,849 B2 | 11/2012 | Gal | 95/158 |
| 8,312,738 B2 | 11/2012 | Singh et al. | 62/629 |
| 8,372,169 B2 | 2/2013 | Tsangaris et al. | 48/120 |
| 8,381,544 B2 | 2/2013 | Coyle | 62/618 |
| 8,388,832 B2 | 3/2013 | Moffett et al. | 208/390 |
| 8,428,835 B2 | 4/2013 | Habert et al. | 701/54 |
| 8,475,572 B2 | 7/2013 | Prast et al. | 95/269 |
| 8,500,105 B2 | 8/2013 | Nieuwoudt | 261/79.2 |
| 8,529,662 B2 | 9/2013 | Kelley et al. | 95/96 |
| 2002/0174687 A1 | 11/2002 | Cai | 65/158 |
| 2002/0189443 A1 | 12/2002 | McGuire | 95/32 |
| 2003/0181772 A1 | 9/2003 | Meyer et al. | 585/324 |
| 2005/0072186 A1* | 4/2005 | Amin | B01D 21/2455 62/601 |
| 2006/0207946 A1 | 9/2006 | McColl et al. | 210/733 |
| 2006/0239879 A1 | 10/2006 | Lallemand et al. | 423/210 |
| 2007/0056317 A1 | 3/2007 | Amin et al. | 62/532 |
| 2007/0144943 A1 | 6/2007 | Lemaire et al. | 208/208 |
| 2007/0277674 A1 | 12/2007 | Hirano et al. | 95/290 |
| 2008/0034789 A1 | 2/2008 | Fieler et al. | 62/623 |
| 2008/0091316 A1 | 4/2008 | Szczublewski | 701/36 |
| 2008/0092589 A1 | 4/2008 | Trainer et al. | 62/640 |
| 2008/0307827 A1 | 12/2008 | Hino et al. | 62/634 |
| 2009/0023605 A1 | 1/2009 | Lebl et al. | 506/27 |
| 2009/0220406 A1 | 9/2009 | Rahman | 423/437.1 |
| 2010/0011809 A1 | 1/2010 | Mak | 62/620 |
| 2010/0018248 A1* | 1/2010 | Fieler | F25J 3/0209 62/617 |
| 2010/0024472 A1 | 2/2010 | Amin et al. | 62/541 |
| 2010/0064725 A1 | 3/2010 | Chieng et al. | 62/620 |
| 2010/0107687 A1 | 5/2010 | Andrian et al. | 62/620 |
| 2010/0132405 A1 | 6/2010 | Nilsen | 62/611 |
| 2010/0147022 A1 | 6/2010 | Hart et al. | 62/601 |
| 2010/0187181 A1 | 7/2010 | Sortwell | 210/726 |
| 2010/0310439 A1 | 12/2010 | Brok et al. | 423/222 |
| 2011/0132034 A1 | 6/2011 | Beaumont et al. | 62/620 |
| 2011/0154856 A1 | 6/2011 | Andrian et al. | 62/618 |
| 2011/0168019 A1 | 7/2011 | Northrop et al. | 95/186 |
| 2011/0192190 A1 | 8/2011 | Andrian et al. | 62/617 |
| 2011/0265512 A1 | 11/2011 | Bearden et al. | 62/617 |
| 2012/0006055 A1 | 1/2012 | Van Santen et al. | 62/618 |
| 2012/0031143 A1 | 2/2012 | Van Santem et al. | 62/617 |
| 2012/0031144 A1 | 2/2012 | Northrop et al. | 62/617 |
| 2012/0079852 A1 | 4/2012 | Northrop et al. | 62/620 |
| 2012/0125043 A1 | 5/2012 | Cullinane et al. | 62/620 |
| 2012/0204599 A1 | 8/2012 | Northrop et al. | 62/617 |
| 2012/0279728 A1 | 11/2012 | Northrop et al. | 166/401 |
| 2013/0032029 A1 | 2/2013 | Mak | 95/94 |
| 2013/0074541 A1 | 3/2013 | Kaminsky et al. | 62/601 |
| 2013/0098105 A1 | 4/2013 | Northrop | 62/617 |
| 2014/0137599 A1 | 5/2014 | Oelfke et al. | 62/619 |

FOREIGN PATENT DOCUMENTS

| | | | |
|---|---|---|---|
| EP | 0508244 | 10/1992 | B01D 53/34 |
| EP | 0 937 488 A2 | 8/1999 | |
| EP | 1338557 | 3/2005 | C01B 17/04 |
| GB | 1010403 | 11/1965 | |
| WO | WO 2002/032536 | 4/2002 | B01F 13/00 |
| WO | WO 2002/039038 | 5/2002 | F25J 3/06 |
| WO | WO 2004/047956 | 6/2004 | B01D 53/14 |
| WO | WO 2008/034789 | 3/2008 | G10K 11/00 |
| WO | WO 2008/095258 | 8/2008 | F25J 3/02 |
| WO | WO 2008/152030 | 12/2008 | B01D 53/00 |
| WO | WO 2009/023605 | 2/2009 | C10G 21/00 |
| WO | WO 2009/029353 | 3/2009 | E21B 43/00 |
| WO | WO 2009/087206 | 7/2009 | B01D 53/00 |
| WO | WO 2009/096370 A1 | 8/2009 | |
| WO | WO 2010/023238 | 3/2010 | F25J 3/06 |
| WO | WO 2010/052299 | 5/2010 | B01D 53/00 |
| WO | WO 2010/136442 | 12/2010 | B01D 53/00 |
| WO | WO 2011/026170 | 3/2011 | C10L 3/10 |
| WO | WO 2013/095828 | 6/2013 | B01D 53/00 |
| WO | WO 2013/142100 | 9/2013 | B03C 3/00 |

OTHER PUBLICATIONS

U.S. Appl. No. 14/516,689, filed Oct. 17, 2014, Cullinane, J. T. et al.
U.S. Appl. No. 14/516,705, filed Oct. 17, 2014, Valencia, J. A. et al.
U.S. Appl. No. 14/516,709, filed Oct. 17, 2014, Valencia, J. A.
U.S. Appl. No. 14/516,713, filed Oct. 17, 2014, Valencia, J. A. et al.
U.S. Appl. No. 14/516,717, filed Oct. 17, 2014, Valencia, J. A. et al.
U.S. Appl. No. 14/516,718, filed Oct. 17, 2014, Valencia, J. A.
U.S. Appl. No. 14/516,726, filed Oct. 17, 2014, Valencia, J. A. et al.
U.S. Appl. No. 14/516,731, filed Oct. 17, 2014, Valencia, J. A. et al.
Aaron, D. et al. (2005) "Separation of $CO_2$ from Flue Gas: A Review," *Separation Science and Technology*, 40, pp. 321-348.
Amin, R. (2003) "Advanced Mini Natural Gas Liquefier," *LNG Journal*, Mar.-Apr. 2003, pp. 20-23.
Black, S. (2006) "Chilled Ammonia Process for CO2 Capture," *Alstom Position Paper*, Nov. 2006, 6 pgs.

(56) References Cited

OTHER PUBLICATIONS

Ciulla, Vincent (2007) "How the Engine Works," About.com, Mar. 21, 2007, [retrieved from the internet on Aug. 17, 2012]. <URL: http://autorepair.about.com/cs/generalinfo/a/aa060500a.html>.

"Cryogenics" *Science Clarified*, May 2, 2006 [retrieved from the internet on Aug. 17, 2012]. <URL: http://www.scienceclarified.com/Co-Di/Cryogenics.html>.

Denton, R. D. et al. (1985) "Integrated Low Temperature Processing of Sour Natural Gas," *Gas Processors Assoc., 64th Ann. Conv.*, pp. 92-96.

Guccione, E. (1963) "New Approach to Recovery of Helium from Natural Gas," *Chem. Engr.*, Sep. 30, 1963, pp. 76-78.

Hassan, S. M. N. (2005) "Techno-Economic Study of $CO_2$ Capture Process for Cement Plants," *University of Waterloo—Thesis*.

Haut, R. C. et al. (1988) "Development and Application of the Controlled Freeze Zone Process," *SPE 17757, SPE Gas Tech. Symp.*—Dallas, TX, pp. 435-443.

Haut, R. C. et al. (1988) "Development and Application of the Controlled Freeze Zone Process," *OSEA 88197, 7th Offshore So. East Asia Conf.*, Singapore, Feb. 1988, pp. 840-848.

Haut, R. C. et al. (1989) "Development and Application of the Controlled Freeze Zone Process," *SPE Production Engineering*, Aug. 1989, pp. 265-271.

Im, U. K. et al. (1971) "Heterogeneous Phase Behavior of Carbon Dioxide in n-Hexane and n-Heptane at Low Temperatures," *Jrnl. of Chem. Engineering Data*, v.16.4, pp. 412-415.

Mitariten, M. et al. (2007) "The Sorbead™ Quick-Cycle Process for Simultaneous Removal of Water, Heavy Hydrocarbons and Mercaptans from Natural Gas," *Laurance Reid Gas Conditioning Conf.*, Feb. 25-27, 2007.

Northrop, P. Scott et al. (2004) "Cryogenic Sour Gas Process Attractive for Acid Gas Injection Applications," *83rd Ann. Gas Processors Assoc. Convention*, New Orleans, LA., pp. 1-8 (XP007912217).

Pagcatipunan, C. et al. (2005) "Maximize the Performance of Spray Nozzle Systems," *CEP Magazine*, Dec. 2005, pp. 38-44.

Reyes, S. C. et al. (1997) "Frequency Modulation Methods for Diffusion and Adsorption Measurements in Porous Solids," *J. Phys. Chem. B*, v.101, pp. 614-622.

Rubin, E. S. et al. (2002) "A Technical, Economic and Environmental Assessment of Amine-based CO2 Capture Technology for Power Plant Greenhouse Gas Control," *U.S. Dept. of Energy*, Oct. 2002, DOE/DE-FC26-00NT40935, 26 pages.

Spero, C. (2007) "Callide Oxyfuel Project," *CS Energy, cLET Seminar*, Jul. 12, 2007, 9 pages.

Thomas, E. R. et al. (1987) "Conceptual Studies Using the Controlled Freeze Zone (CFZ) Process," *AIChE Summer Nat'l Mtg.*, Aug. 16-19, 1987.

Thomas, E. R. et al. (1988) "Conceptual Studies for $CO_2$/Natural Gas Separation Using the Control Freeze Zone (CFZ) Process," *as Separation and Purification*, v. 2, pp. 84-89.

Valencia, J. A. et al. (2008) "Controlled Freeze Zone™ Technology for Enabling Processing of High $CO_2$ and $H_2S$ Gas Reserves," SPE-IPTC 12708, Kuala Lumpur, IN, v.4.1, Jan. 2008, pp. 2358-2363.

Victory, D. J. et al. (1987) "The CFZ Process: Direct Methane-Carbon Dioxide Fractionation," *66th Ann. GPA Convention*, Mar. 16-18, Denver, CO.

Wilson, R.W. et al. (1968) "Helium: Its Extraction and Purification," *Journ. Petrol. Tech.*, v. 20, pp. 341-344.

\* cited by examiner

METHOD AND DEVICE FOR SEPARATING HYDROCARBONS AND CONTAMINANTS WITH A SPRAY ASSEMBLY

CROSS REFERENCE TO RELATED APPLICATIONS

This application is related to U.S. Patent Application No. 61/912,957 filed Dec. 6, 2013 entitled METHOD AND DEVICE FOR SEPARATING HYDROCARBONS AND CONTAMINANTS WITH A SPRAY ASSEMBLY, and U.S. Patent Application No. 62/044,770 filed Sep. 2, 2014 entitled METHOD AND DEVICE FOR SEPARATING HYDROCARBONS AND CONTAMINANTS WITH A SPRAY ASSEMBLY, the entirety of which is incorporated by reference herein.

This application is related to but does not claim priority to U.S. Provisional patent application No. 61/912,959 filed on Dec. 6, 2013 entitled METHOD AND SYSTEM OF MAINTAINING A LIQUID LEVEL IN A DISTILLATION TOWER; 61/912,964 filed on Dec. 6, 2013 entitled METHOD AND DEVICE FOR SEPARATING A FEED STREAM USING RADIATION DETECTORS; 61/912,970 filed on Dec. 6, 2013 entitled METHOD AND SYSTEM OF DEHYDRATING A FEED STREAM PROCESSED IN A DISTILLATION TOWER; 61/912,975 filed on Dec. 6, 2013 entitled METHOD AND SYSTEM FOR SEPARATING A FEED STREAM WITH A FEED STREAM DISTRIBUTION MECHANISM; 61/912,978 filed on Dec. 6, 2013 entitled METHOD AND SYSTEM FOR PREVENTING ACCUMULATION OF SOLIDS IN A DISTILLATION TOWER; 61/912,983 filed on Dec. 6, 2013 entitled METHOD OF REMOVING SOLIDS BY MODIFYING A LIQUID LEVEL IN A DISTILLATION TOWER; 61/912,984 filed on Dec. 6, 2013 entitled METHOD AND SYSTEM OF MODIFYING A LIQUID LEVEL DURING START-UP OPERATIONS; 61/912,986 filed on Dec. 6, 2013 entitled METHOD AND DEVICE FOR SEPARATING HYDROCARBONS AND CONTAMINANTS WITH A HEATING MECHANISM TO DESTABILIZE AND/OR PREVENT ADHESION OF SOLIDS; 61/912,987 filed on Dec. 6, 2013 entitled METHOD AND DEVICE FOR SEPARATING HYDROCARBONS AND CONTAMINANTS WITH A SURFACE TREATMENT MECHANISM.

BACKGROUND

Fields of Disclosure

The disclosure relates generally to the field of fluid separation. More specifically, the disclosure relates to the cryogenic separation of contaminants, such as acid gas, from a hydrocarbon.

This section is intended to introduce various aspects of the art, which may be associated with the present disclosure. This discussion is intended to provide a framework to facilitate a better understanding of particular aspects of the present disclosure. Accordingly, it should be understood that this section should be read in this light, and not necessarily as admissions of prior art.

The production of natural gas hydrocarbons, such as methane and ethane, from a reservoir oftentimes carries with it the incidental production of non-hydrocarbon gases. Such gases include contaminants, such as at least one of carbon dioxide ("$CO_2$"), hydrogen sulfide ("$H_2S$"), carbonyl sulfide, carbon disulfide and various mercaptans. When a feed stream being produced from a reservoir includes these contaminants mixed with hydrocarbons, the stream is oftentimes referred to as "sour gas."

Many natural gas reservoirs have relatively low percentages of hydrocarbons and relatively high percentages of contaminants. Contaminants may act as a diluent and lower the heat content of the gas stream. Some contaminants, like sulfur-bearing compounds, are noxious and may even be lethal. Additionally, in the presence of water some contaminants can become quite corrosive.

It is desirable to remove contaminants from a stream containing hydrocarbons to produce sweet and concentrated hydrocarbons. Specifications for pipeline quality natural gas typically call for a maximum of 2-4% $CO_2$ and ¼ grain $H_2S$ per 100 scf (4 ppmv) or 5 mg/Nm3 $H_2S$. Specifications for lower temperature processes such as natural gas liquefaction plants or nitrogen rejection units typically require less than 50 ppm $CO_2$.

The separation of contaminants from hydrocarbons is difficult and consequently significant work has been applied to the development of hydrocarbon/contaminant separation methods. These methods can be placed into three general classes: absorption by solvents (physical, chemical and hybrids), adsorption by solids, and distillation.

Separation by distillation of some mixtures can be relatively simple and, as such, is widely used in the natural gas industry. However, distillation of mixtures of natural gas hydrocarbons, primarily methane, and one of the most common contaminants in natural gas, carbon dioxide, can present significant difficulties. Conventional distillation principles and conventional distillation equipment are predicated on the presence of only vapor and liquid phases throughout the distillation tower. The separation of $CO_2$ from methane by distillation involves temperature and pressure conditions that result in solidification of $CO_2$ if a pipeline or better quality hydrocarbon product is desired. The required temperatures are cold temperatures typically referred to as cryogenic temperatures.

Certain cryogenic distillations can overcome the above mentioned difficulties. These cryogenic distillations provide the appropriate mechanism to handle the formation and subsequent melting of solids during the separation of solid-forming contaminants from hydrocarbons. The formation of solid contaminants in equilibrium with vapor-liquid mixtures of hydrocarbons and contaminants at particular conditions of temperature and pressure takes place in a controlled freeze zone section.

Sometimes solids can adhere to an internal (e.g., controlled freeze zone wall) of the controlled freeze zone section rather than falling to the bottom of the controlled freeze zone section.

The adherence is disadvantageous. The adherence, if uncontrolled, can interfere with the proper operation of the controlled freeze zone section and the effective separation of methane from the contaminants.

A need exists for improved technology to separate a feed stream, containing hydrocarbons and contaminants, while also preventing the adherence of solids on the controlled freeze zone wall.

SUMMARY

The present disclosure provides a device and method for separating contaminants from hydrocarbons and preventing the adherence of solids on the controlled freeze zone wall, among other things.

A method for separating a feed stream in a distillation tower comprising maintaining a controlled freeze zone section in the distillation tower, receiving a freezing zone liquid stream in a spray nozzle assembly in the controlled freeze zone section, wherein the spray nozzle assembly comprises a plurality of outer spray nozzles on an outer periphery of the spray nozzle assembly and at least one inner spray nozzle interior to the plurality of outer spray nozzles, wherein each outer spray nozzle is configured to spray the freezing zone liquid stream along a central spray axis, and wherein the central spray axis of at least one of the plurality of outer spray nozzles is not parallel to a controlled freeze zone wall, and spraying the freezing zone liquid stream through the spray nozzle assembly into the controlled freeze zone section at a temperature and pressure at which the solid and the hydrocarbon-enriched vapor stream form.

A method for producing hydrocarbons comprising maintaining a controlled freeze zone section in the distillation tower that receives a freezing zone liquid stream to form a solid and a hydrocarbon-enriched vapor stream in the controlled freeze zone section, maintaining a spray assembly in the controlled freeze zone section, wherein the spray assembly comprises a first type of spray nozzle on an outer periphery and a second type of spray nozzle interior to the first type of spray nozzle, and wherein the first type of spray nozzle orients spray at an angle with respect to a controlled freeze zone wall so as to minimize spray liquid impingement on the controlled freeze zone wall, injecting the freezing zone liquid stream into the controlled freeze zone section through the spray assembly at a temperature and pressure at which the solid and the hydrocarbon-enriched vapor stream form, wherein the freezing zone liquid stream comprises a freezing zone liquid stream outermost portion, and producing the hydrocarbon-enriched vapor stream extracted from the distillation tower.

A distillation tower that separates a contaminant in a feed stream from a hydrocarbon in the feed stream may comprise a controlled freeze zone section comprising a controlled freeze zone section comprising a controlled freeze zone wall, a first type of spray nozzle configured to inject a freezing zone liquid stream into the controlled freeze zone section at a temperature and pressure at which a solid forms, and a melt tray assembly below the first type of spray nozzle that configured to melt the solid that comprises the contaminant, wherein the first type of spray nozzle is configured to direct a freezing zone liquid stream outermost portion at an angle to the controlled freeze zone wall with the first type of spray nozzle, and wherein the angle is calculated to minimize or eliminate impingement of the freezing zone liquid stream on the controlled freeze zone wall.

The foregoing has broadly outlined the features of the present disclosure so that the detailed description that follows may be better understood. Additional features will also be described herein.

BRIEF DESCRIPTION OF THE DRAWINGS

These and other features, aspects and advantages of the disclosure will become apparent from the following description, appending claims and the accompanying drawings, which are briefly described below.

Figure 1:
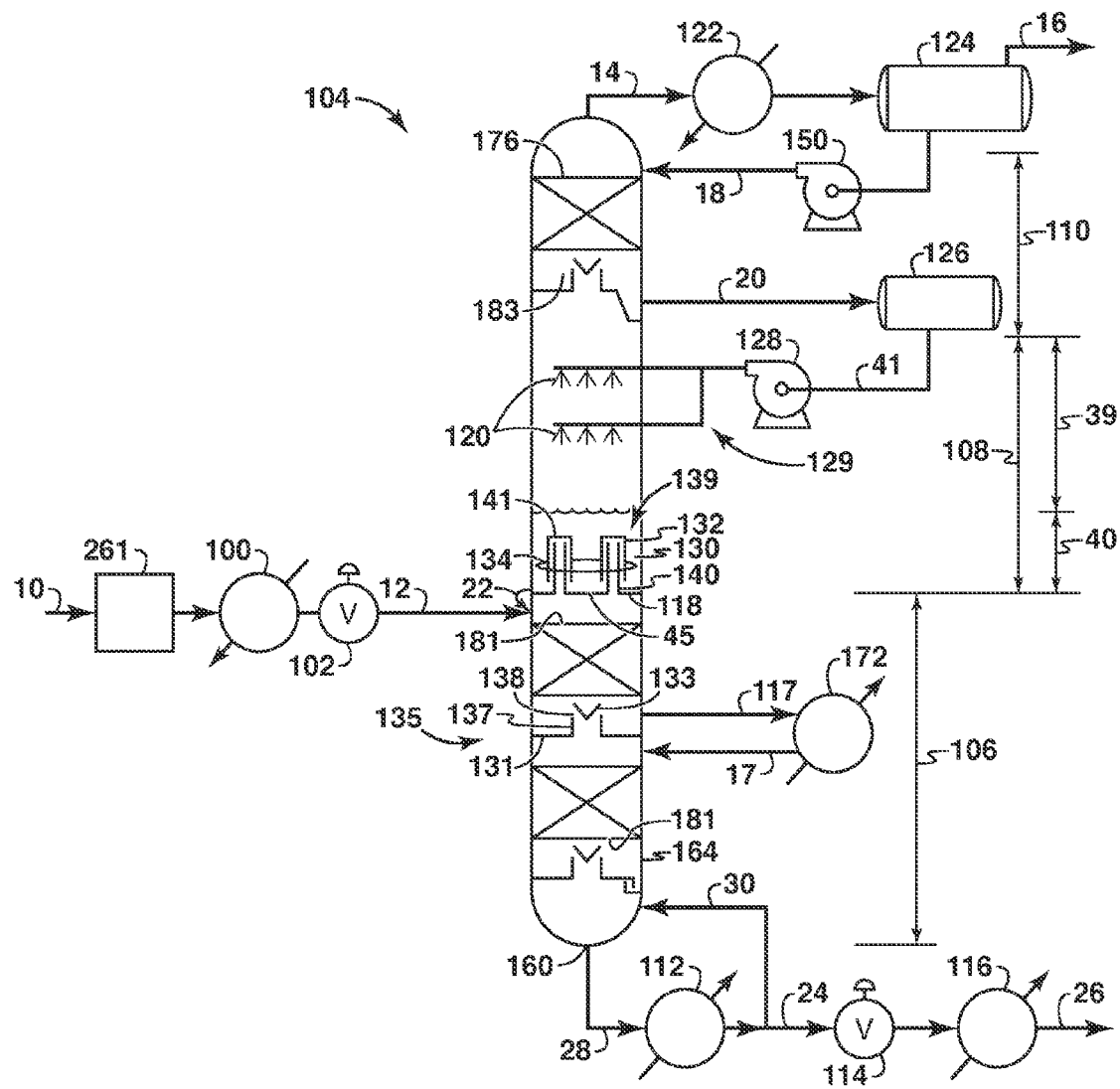
FIG. 1 is a schematic diagram of a tower with sections within a single vessel.

It should be noted that the figures are merely examples and no limitations on the scope of the present disclosure are intended thereby. Further, the figures are generally not drawn to scale, but are drafted for purposes of convenience and clarity in illustrating various aspects of the disclosure.

DETAILED DESCRIPTION

For the purpose of promoting an understanding of the principles of the disclosure, reference will now be made to the features illustrated in the drawings and specific language will be used to describe the same. It will nevertheless be understood that no limitation of the scope of the disclosure is thereby intended. Any alterations and further modifications, and any further applications of the principles of the disclosure as described herein are contemplated as would normally occur to one skilled in the art to which the disclosure relates. It will be apparent to those skilled in the relevant art that some features that are not relevant to the present disclosure may not be shown in the drawings for the sake of clarity.

As referenced in this application, the terms "stream," "gas stream," "vapor stream," and "liquid stream" refer to different stages of a feed stream as the feed stream is processed in a distillation tower that separates methane, the primary hydrocarbon in natural gas, from contaminants. Although the phrases "gas stream," "vapor stream," and "liquid stream," refer to situations where a gas, vapor, and liquid is mainly present in the stream, respectively, there may be other phases also present within the stream. For example, a gas may also be present in a "liquid stream." In some instances, the terms "gas stream" and "vapor stream" may be used interchangeably.

The disclosure relates to a system and method for separating a feed stream in a distillation tower. The system and method helps prevent the formation of solids that adhere to the wall of the controlled freeze zone section by directing a freezing zone liquid stream outermost portion of a first type of spray nozzle at an outer periphery of the spray assembly so as to eliminate, reduce, and/or minimize spray liquid impingement on the controlled freeze zone wall of the controlled freeze zone section. FIGS. 1-7 of the disclosure display various aspects of the system and method.

The system and method may separate a feed stream having methane and contaminants. The system may comprise a distillation tower 104, 204 (FIGS. 1-4). The distillation tower 104, 204 may separate the contaminants from the methane.

The distillation tower 104, 204 may be separated into three functional sections: a lower section 106, a middle controlled freeze zone section 108 and an upper section 110. The distillation tower 104, 204 may incorporate three functional sections when the upper section 110 is needed and/or desired.

The distillation tower 104, 204 may incorporate only two functional sections when the upper section 110 is not needed and/or desired. When the distillation tower does not include an upper section 110, a portion of vapor leaving the middle controlled freeze zone section 108 may be condensed in a condenser 122 and returned as a liquid stream via a spray assembly 129. Moreover, lines 18 and 20 may be eliminated, elements 124 and 126 may be one and the same, and elements 150 and 128 may be one and the same. The stream in line 14, now taking the vapors leaving the middle controlled freeze section 108, directs these vapors to the condenser 122.

The lower section 106 may also be referred to as a stripper section. The middle controlled freeze zone section 108 may also be referred to as a controlled freeze zone section. The upper section 110 may also be referred to as a rectifier section.

Figure 3:
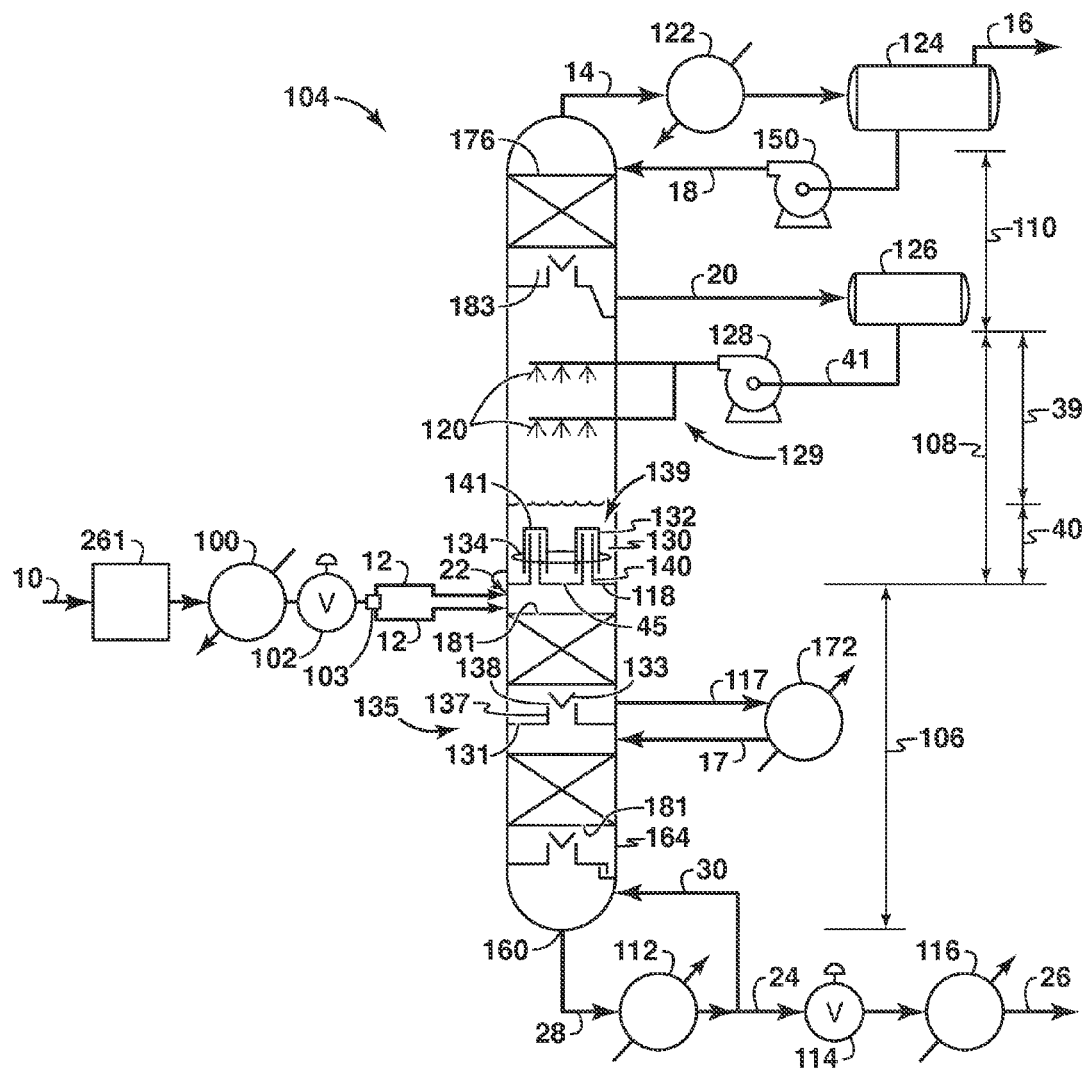
FIG. 3 is a schematic diagram of a tower with sections within a single vessel.

The sections of the distillation tower 104 may be housed within a single vessel (FIGS. 1 and 3). For example, the lower section 106, the middle controlled freeze zone section 108, and the upper section 110 may be housed within a single vessel 164.

Figure 2:
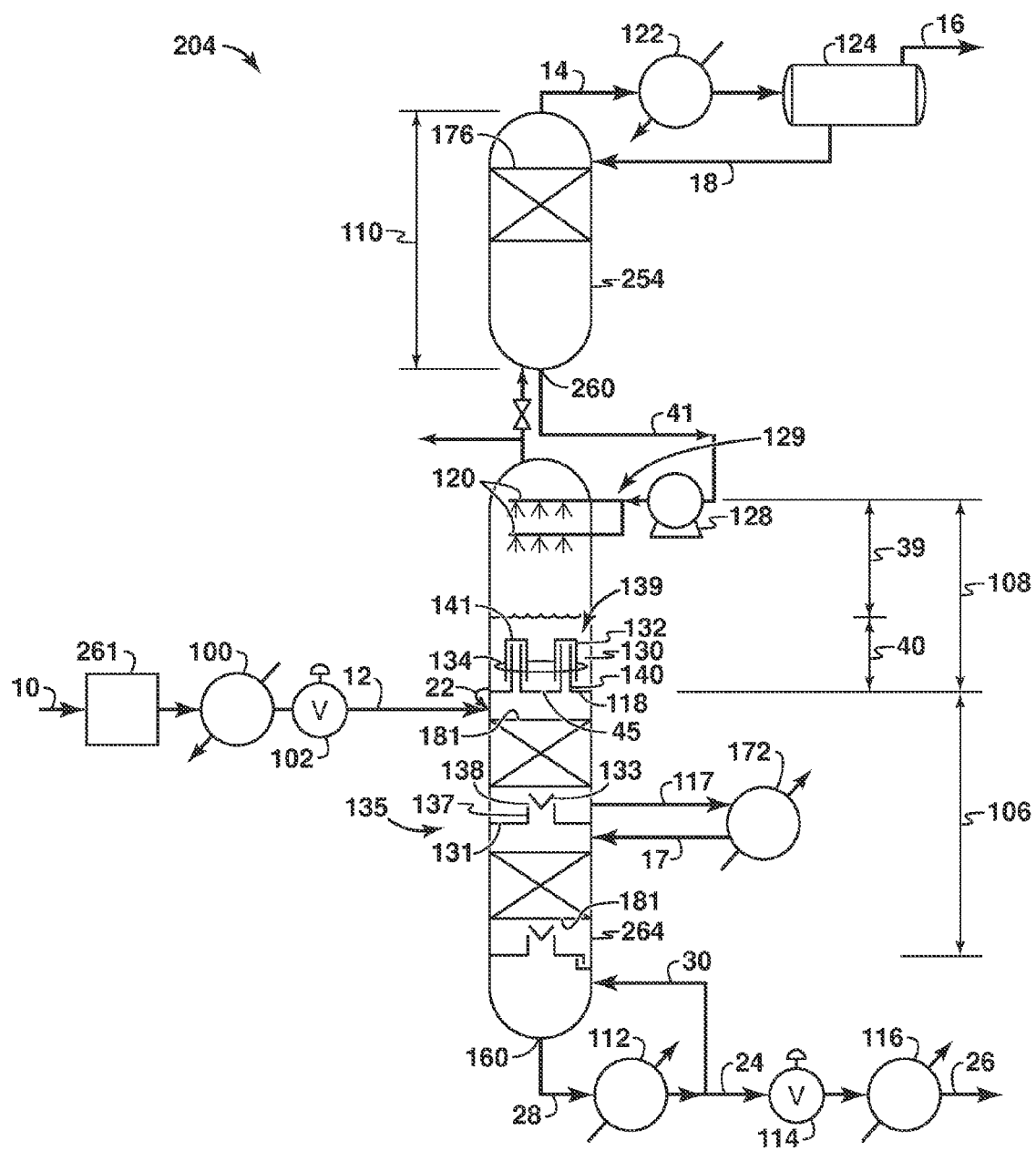
FIG. 2 is a schematic diagram of a tower with sections within multiple vessels.
Figure 4:
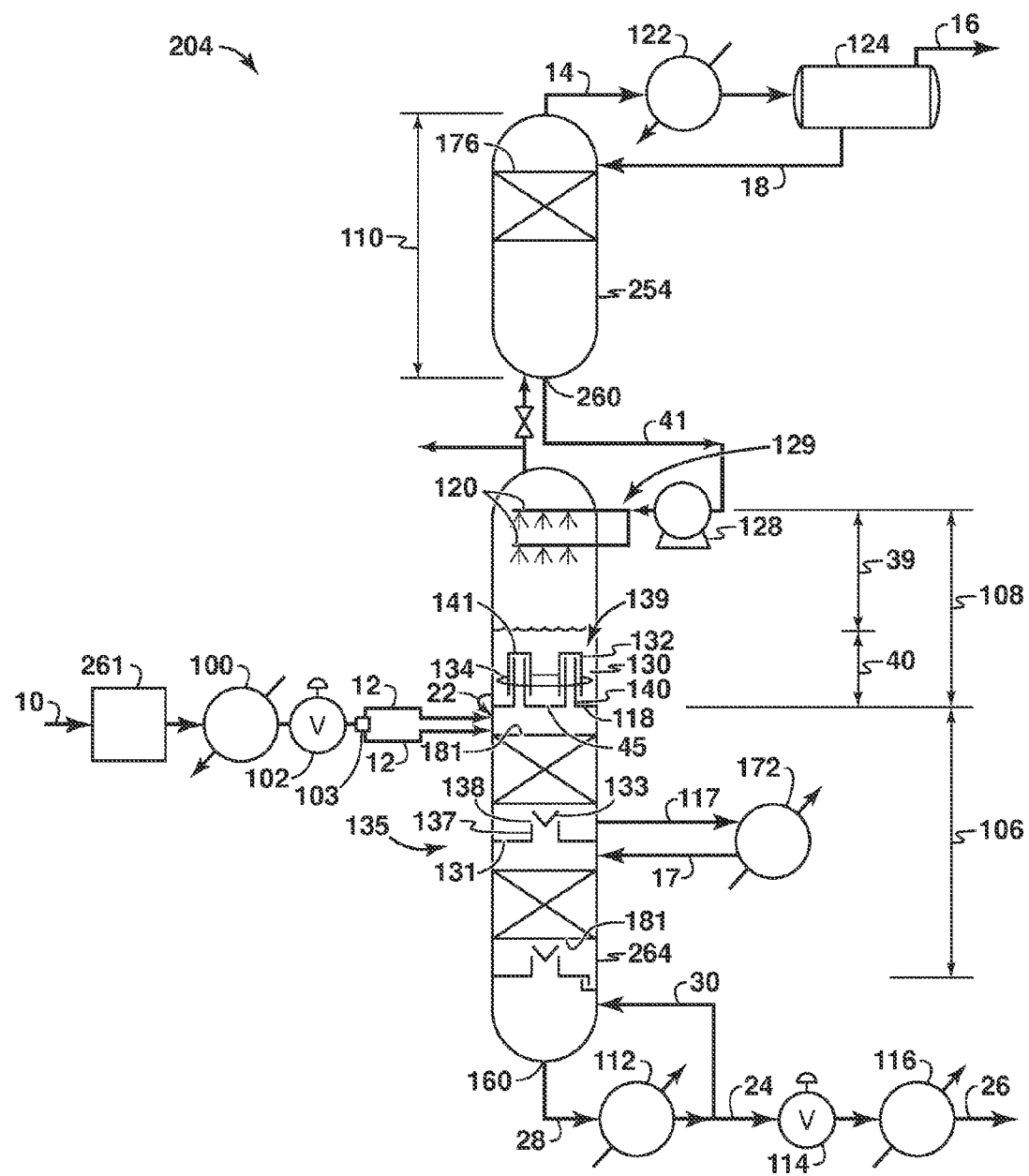
FIG. 4 is a schematic diagram of a tower with sections within multiple vessels.

The sections of the distillation tower 204 may be housed within a plurality of vessels to form a split-tower configuration (FIGS. 2 and 4). Each of the vessels may be separate from the other vessels. Piping and/or another suitable mechanism may connect one vessel to another vessel. In this instance, the lower section 106, middle controlled freeze zone section 108 and upper section 110 may be housed within two or more vessels. For example, as shown in FIGS. 2 and 4, the upper section 110 may be housed within a single vessel 254 and the lower and middle controlled freeze sections 106, 108 may be housed within a single vessel 264. When this is the case, a liquid stream exiting the upper section 110, may exit through a liquid outlet bottom 260. The liquid outlet bottom 260 is at the bottom of the upper section 110. Although not shown, each of the sections may be housed within its own separate vessel, or one or more section may be housed within separate vessels, or the upper and middle controlled freeze zone sections may be housed within a single vessel and the lower section may be housed within a single vessel, etc. When sections of the distillation tower are housed within vessels, the vessels may be side-by-side along a horizontal line and/or above each other along a vertical line.

The split-tower configuration may be beneficial in situations where the height of the distillation tower, motion considerations, and/or transportation issues, such as for remote locations, need to be considered. This split-tower configuration allows for the independent operation of one or more sections. For example, when the upper section is housed within a single vessel and the lower and middle controlled freeze zone sections are housed within a single vessel, independent generation of reflux liquids using a substantially contaminant-free, largely hydrocarbon stream from a packed gas pipeline or an adjacent hydrocarbon line, may occur in the upper section. And the reflux may be used to cool the upper section, establish an appropriate temperature profile in the upper section, and/or build up liquid inventory at the bottom of the upper section to serve as an initial source of spray liquids for the middle controlled freeze zone section. Moreover, the middle controlled freeze zone and lower sections may be independently prepared by chilling the feed stream, feeding it to the optimal location be that in the lower section or in the middle controlled freeze zone section, generating liquids for the lower and the middle controlled freeze zone sections, and disposing the vapors off the middle controlled freeze zone section while they are off specification with too high a contaminant content. Also, liquid from the upper section may be intermittently or continuously sprayed, building up liquid level in the bottom of the middle controlled freeze zone section and bringing the contaminant content in the middle controlled freeze zone section down and near steady state level so that the two vessels may be connected to send the vapor stream from the middle controlled freeze zone section to the upper section, continuously spraying liquid from the bottom of the upper section into the middle controlled freeze zone section and stabilizing operations into steady state conditions. The split tower configuration may utilize a sump of the upper section as a liquid receiver for the pump 128, therefore obviating the need for a liquid receiver 126 in FIGS. 1 and 3.

The system may also include a heat exchanger 100 (FIGS. 1-4). The feed stream 10 may enter the heat exchanger 100 before entering the distillation tower 104, 204. The feed stream 10 may be cooled within the heat exchanger 100. The heat exchanger 100 helps drop the temperature of the feed stream 10 to a level suitable for introduction into the distillation tower 104, 204.

The system may include an expander device 102 (FIGS. 1-4). The feed stream 10 may enter the expander device 102 before entering the distillation tower 104, 204. The feed stream 10 may be expanded in the expander device 102 after exiting the heat exchanger 100. The expander device 102 helps drop the temperature of the feed stream 10 to a level suitable for introduction into the distillation tower 104, 204. The expander device 102 may be any suitable device, such as a valve. If the expander device 102 is a valve, the valve may be any suitable valve that may aid in cooling the feed stream 10 before it enters the distillation tower 104, 204. For example, the valve 102 may comprise a Joule-Thompson (J-T) valve.

The system may include a feed separator 103 (FIGS. 3-4). The feed stream may enter the feed separator before entering the distillation tower 104, 204. The feed separator may separate a feed stream having a mixed liquid and vapor stream into a liquid stream and a vapor stream. Lines 12 may extend from the feed separator to the distillation tower 104, 204. One of the lines 12 may receive the vapor stream from the feed separator. Another one of the lines 12 may receive the liquid stream from the feed separator. Each of the lines 12 may extend to the same and/or different sections (i.e. middle controlled freeze zone, and lower sections) of the distillation tower 104, 204. The expander device 102 may or may not be downstream of the feed separator 103. The expander device 102 may comprise a plurality of expander devices 102 such that each line 12 has an expander device 102.

The system may include a dehydration unit 261 (FIGS. 1-4). The feed stream 10 may enter the dehydration unit 261 before entering the distillation tower 104, 204. The feed stream 10 enters the dehydration unit 261 before entering the heat exchanger 100 and/or the expander device 102. The dehydration unit 261 removes water from the feed stream 10 to prevent water from later presenting a problem in the heat exchanger 100, expander device 102, feed separator 103, or distillation tower 104, 204. The water can present a problem by forming a separate water phase (i.e., ice and/or hydrate) that plugs lines, equipment or negatively affects the distillation process. The dehydration unit 261 dehydrates the feed stream to a dew point sufficiently low to ensure a separate water phase will not form at any point downstream during the rest of the process. The dehydration unit may be any suitable dehydration mechanism, such as a molecular sieve or a glycol dehydration unit.

The system may include a filtering unit (not shown). The feed stream 10 may enter the filtering unit before entering the distillation tower 104, 204. The filtering unit may remove undesirable contaminants from the feed stream before the feed stream enters the distillation tower 104, 204. Depending on what contaminants are to be removed, the filtering unit may be before or after the dehydration unit 261 and/or before or after the heat exchanger 100.

The systems may include a line 12 (FIGS. 1-4). The line may also be referred to as an inlet channel 12. The feed stream 10 may be introduced into the distillation tower 104, 204 through the line 12. The line 12 may extend to the lower section 106 or the middle controlled freeze zone section 108 of the distillation tower 104, 204. For example, the line 12 may extend to the lower section 106 such that the feed stream 10 may enter the lower section 106 of the distillation tower 104, 204 (FIGS. 1-4). The line 12 may directly or indirectly extend to the lower section 106 or the middle controlled freeze zone section 108. The line 12 may extend to an outer surface of the distillation tower 104, 204 before entering the distillation tower 104, 204.

If the system includes the feed separator 103 (FIGS. 3-4), the line 12 may comprise a plurality of lines 12. Each line may be the same line as one of the lines that extends from the feed separator to a specific portion of the distillation tower 104, 204.

The lower section 106 is constructed and arranged to separate the feed stream 10 into an enriched contaminant bottom liquid stream (i.e., liquid stream) and a freezing zone vapor stream (i.e., vapor stream). The lower section 106 separates the feed stream at a temperature and pressure at which no solids form. The liquid stream may comprise a greater quantity of contaminants than of methane. The vapor stream may comprise a greater quantity of methane than of contaminants. In any case, the vapor stream is lighter than the liquid stream. As a result, the vapor stream rises from the lower section 106 and the liquid stream falls to the bottom of the lower section 106.

The lower section 106 may include and/or connect to equipment that separates the feed stream. The equipment may comprise any suitable equipment for separating methane from contaminants, such as one or more packed sections 181, or one or more distillation trays with perforations, downcomers, and weirs (FIGS. 1-4).

The equipment may include components that apply heat to the stream to form the vapor stream and the liquid stream. For example, the equipment may comprise a first reboiler 112 that applies heat to the stream. The first reboiler 112 may be located outside of the distillation tower 104, 204. The equipment may also comprise a second reboiler 172 that applies heat to the stream. The second reboiler 172 may be located outside of the distillation tower 104, 204. Line 117 may lead from the distillation tower to the second reboiler 172. Line 17 may lead from the second reboiler 172 to the distillation tower. Additional reboilers, set up similarly to the second reboiler described above, may also be used.

The first reboiler 112 may apply heat to the liquid stream that exits the lower section 106 through a liquid outlet 160 of the lower section 106. The liquid stream may travel from the liquid outlet 160 through line 28 to reach the first reboiler 112 (FIGS. 1-4). The amount of heat applied to the liquid stream by the first reboiler 112 can be increased to separate more methane from contaminants. The more heat applied by the reboiler 112 to the stream, the more methane separated from the liquid contaminants, though more contaminants will also be vaporized.

The first reboiler 112 may also apply heat to the stream within the distillation tower 104, 204. Specifically, the heat applied by the first reboiler 112 warms up the lower section 106. This heat travels up the lower section 106 and supplies heat to warm solids entering a melt tray assembly 139 (FIGS. 1-4) of the middle controlled freeze zone section 108 so that the solids form a liquid and/or slurry mix.

The second reboiler 172 may apply heat to the stream within the lower section 106. This heat may be applied closer to the middle controlled freeze zone section 108 than the heat applied by the first reboiler 112. As a result, the heat applied by the second reboiler 172 reaches the middle controlled freeze zone section 108 faster than the heat applied by the first reboiler 112. The second reboiler 172 may also help with energy integration. Some commercial applications may not have this second reboiler 172.

The equipment may include one or more chimney assemblies 135 (FIGS. 1-4). While falling to the bottom of the lower section 106, the liquid stream may encounter one or more of the chimney assemblies 135.

Each chimney assembly 135 includes a chimney tray 131 that collects the liquid stream within the lower section 106. The liquid stream that collects on the chimney tray 131 may be fed to the second reboiler 172. After the liquid stream is heated in the second reboiler 172, the stream may return to the middle controlled freeze zone section 106 to supply heat to the middle controlled freeze zone section 106 and/or the melt tray assembly 139. Unvaporized (or partially vaporized) stream exiting the second reboiler 172 may be fed back to the distillation tower 104, 204 below the chimney tray 131. Vapor stream exiting the second reboiler 172 may be routed under or above the chimney tray 131 when the vapor stream enters the distillation tower 104, 204.

The chimney tray 131 may include one or more chimneys 137. The chimney 137 serves as a channel that the vapor stream in the lower section 106 traverses. The vapor stream travels through an opening in the chimney tray 131 at the bottom of the chimney 137 to the top of the chimney 137. In the depicted embodiment, the opening is closer to the bottom of the lower section 106 than it is to the bottom of the middle controlled freeze zone section 108. The top is closer to the bottom of the middle controlled freeze zone section 108 than it is to the bottom of the lower section 106.

Each chimney 137 has attached to it a chimney cap 133. The chimney cap 133 covers a chimney top opening 138 of the chimney 137. The chimney cap 133 prevents the liquid stream from entering the chimney 137. The vapor stream exits the chimney assembly 135 via the chimney top opening 138.

After falling to the bottom of the lower section 106, the liquid stream exits the distillation tower 104, 204 through the liquid outlet 160. The liquid outlet 160 is within the lower section 106 (FIGS. 1-4). The liquid outlet 160 may be located at the bottom of the lower section 106.

After exiting through the liquid outlet 160, the feed stream may travel via line 28 to the first reboiler 112. The feed stream may be heated by the first reboiler 112 and vapor may then re-enter the lower section 106 through line 30. Unvaporized liquid may continue out of the distillation process via line 24.

The system may include an expander device 114 (FIGS. 1-4). After entering line 24, the heated liquid stream may be expanded in the expander device 114. The expander device 114 may be any suitable device, such as a valve. The valve 114 may be any suitable valve, such as a J-T valve.

The system may include a heat exchanger 116 (FIGS. 1-4). The liquid stream heated by the first reboiler 112 may be cooled or heated by the heat exchanger 116. The heat exchanger 116 may be a direct heat exchanger or an indirect heat exchanger. The heat exchanger 116 may comprise any suitable heat exchanger.

Figure 7:
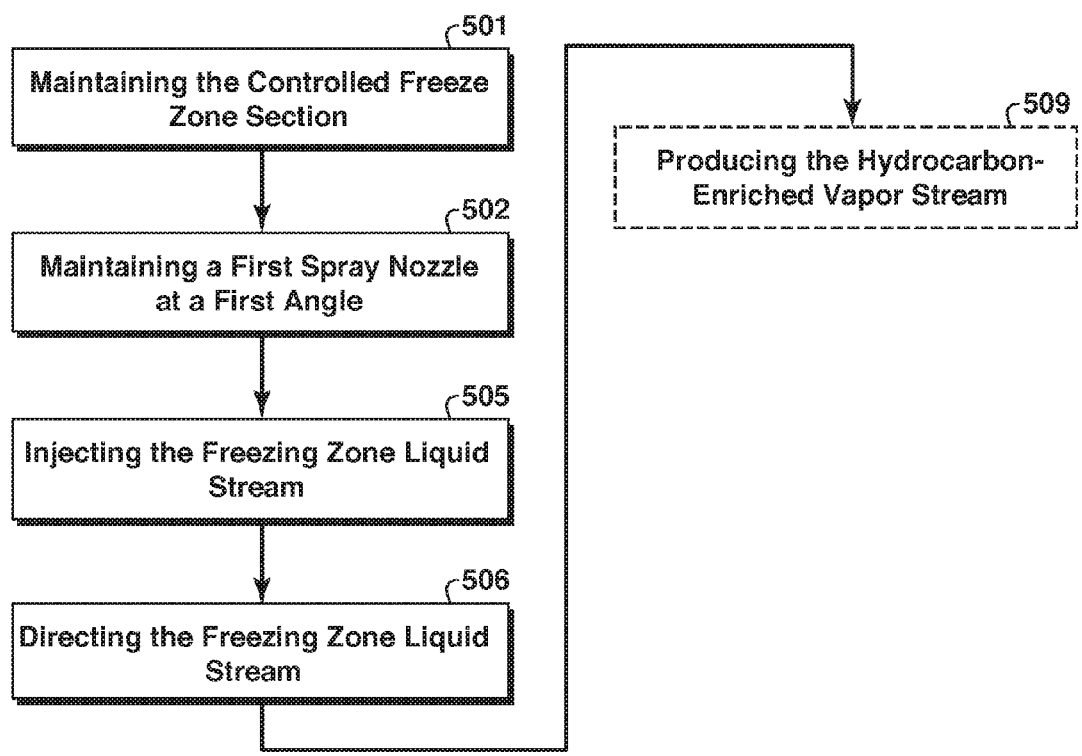
FIG. 7 is a flowchart of a method within the scope of the present disclosure.

The vapor stream in the lower section 106 rises from the lower section 106 to the middle controlled freeze zone section 108. The middle controlled freeze zone section 108 is maintained to receive a freezing zone liquid stream to form the solid and the vapor stream (i.e., hydrocarbon-enriched vapor stream) in the middle controlled freeze zone section 108, 501 (FIG. 7). The middle controlled freeze zone section 108 is constructed and arranged to separate the feed stream 10 introduced into the middle controlled freeze zone section into a solid and a vapor stream. The solid and the vapor stream are formed in the middle controlled freeze zone section 108 when the freezing zone liquid stream is injected into the middle controlled freeze zone section 108 at a temperature and pressure at which the solid and vapor stream form, 505 (FIG. 7). The solid may be comprised more of contaminants than of methane. The vapor stream may comprise more methane than contaminants.

Figure 5:
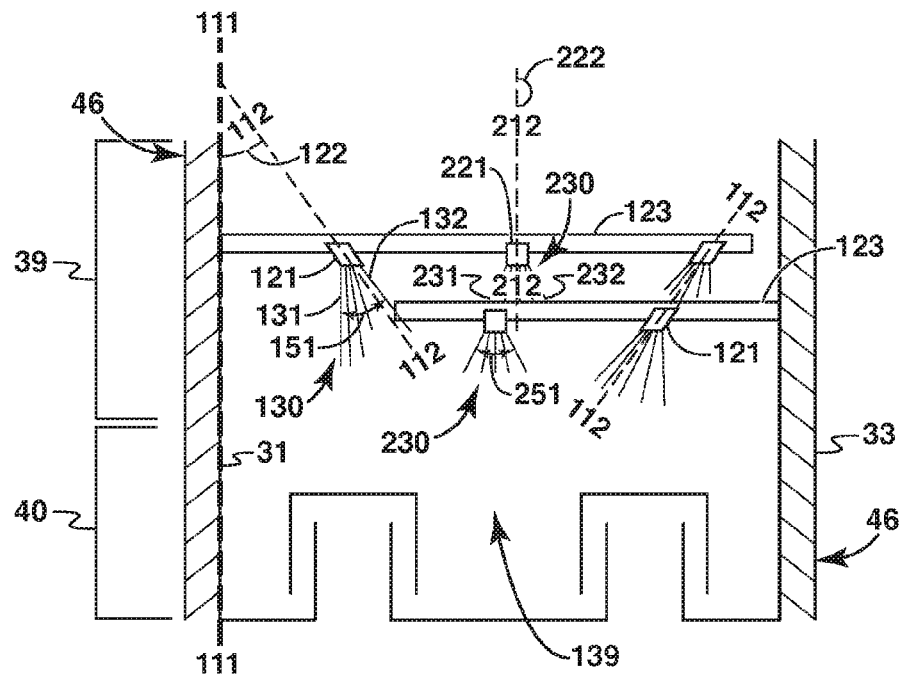
FIG. 5 is a schematic, cross-sectional diagram of a controlled freeze zone section.

The middle controlled freeze zone section 108 includes a lower section 40 and an upper section 39 (FIG. 5). The lower section 40 is below the upper section 39. The lower section 40 directly abuts the upper section 39. The lower section 40 is primarily but may not exclusively be a heating section of the middle controlled freeze zone section 108. The upper section 39 is primarily but may not exclusively be a cooling section of the middle controlled freeze zone section 108. The temperature and pressure of the upper section 39 are chosen so that the solid can form in the middle controlled freeze zone section 108.

The middle controlled freeze zone section 108 may comprise a melt tray assembly 139 that is maintained in the middle controlled freeze zone section 108 (FIGS. 1-5). The melt tray assembly 139 is within the lower section 40 of the middle controlled freeze zone section 108. The melt tray assembly 139 is not within the upper section 39 of the middle controlled freeze zone section 108.

The melt tray assembly 139 is constructed and arranged to melt a solid formed in the middle controlled freeze zone section 108. When the warm vapor stream rises from the lower section 106 to the middle controlled freeze zone section 108, the vapor stream immediately encounters the melt tray assembly 139 and supplies heat to melt the solid. The melt tray assembly 139 may comprise at least one of a melt tray 118, a bubble cap 132, a liquid 130 and heat mechanism(s) 134.

The melt tray 118 may collect a liquid and/or slurry mix. The melt tray 118 divides at least a portion of the middle controlled freeze zone section 108 from the lower section 106. The melt tray 118 is at the bottom 45 of the middle controlled freeze zone section 108.

One or more bubble caps 132 may act as a channel for the vapor stream rising from the lower section 106 to the middle controlled freeze zone section 108. The bubble cap 132 may provide a path for the vapor stream up the riser 140 and then down and around the riser 140 to the melt tray 118. The riser 140 is covered by a cap 141. The cap 140 prevents the liquid 130 from travelling into the riser 140. The cap 141 helps prevent solids from travelling into the riser 140. The vapor stream's traversal through the bubble cap 132 allows the vapor stream to transfer heat to the liquid 130 within the melt tray assembly 139.

One or more heat mechanisms 134 may further heat up the liquid 130 to facilitate melting of the solids into a liquid and/or slurry mix. The heat mechanism(s) 134 may be located anywhere within the melt tray assembly 139. For example, as shown in FIGS. 1-4, a heat mechanism 134 may be located around the bubble caps 132. The heat mechanism 134 may be any suitable mechanism, such as a heat coil. The heat source of the heat mechanism 134 may be any suitable heat source.

The liquid 130 in the melt tray assembly is heated by the vapor stream. The liquid 130 may also be heated by the one or more heat mechanisms 134. The liquid 130 helps melt the solids formed in the middle controlled freeze zone section 108 into a liquid and/or slurry mix. Specifically, the heat transferred by the vapor stream heats up the liquid, thereby enabling the heat to melt the solids. The liquid 130 is at a level sufficient to melt the solids.

The middle controlled freeze zone section 108 may also comprise a spray assembly 129. The spray assembly 129 cools the vapor stream that rises from the lower section 40. The spray assembly 129 sprays liquid, which is cooler than the vapor stream, on the vapor stream to cool the vapor stream. The spray assembly 129 is within the upper section 39. The spray assembly 129 is not within the lower section 40. The spray assembly 129 is above the melt tray assembly 139. In other words, the melt tray assembly 139 is below the spray assembly 129.

Figure 6:
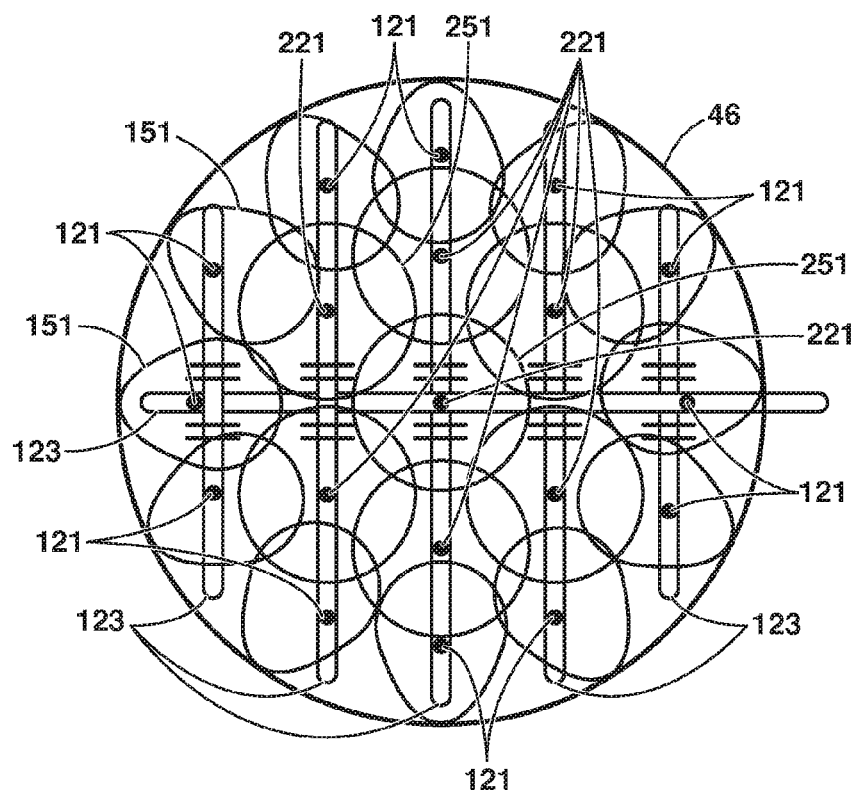
FIG. 6 is a top view of a spray assembly.

As shown in FIGS. 5-6, the spray assembly 129 includes a plurality of spray nozzles 121, 221. The plurality of spray nozzles 121, 221 comprise a plurality of outer spray nozzles on an outer periphery of the spray nozzle assembly, e.g., a first type of spray nozzle 121, and at least one inner spray nozzle interior to the plurality of outer spray nozzles, e.g., a second type of spray nozzle 221. The first type of spray nozzle 121 may be maintained in the controlled freeze zone section 108 at a first angle 122, 502 (FIG. 5-7) about its axis 112-112 with a spray distribution 151 (added to FIG. 5). The second type of spray nozzle 221 may be maintained in the controlled freeze zone section 108 at a second angle 222 about its axis 212-212 with a spray distribution 251 (added to FIG. 5).

There may be any suitable amount of first type of spray nozzles 121 and/or second type of spray nozzles 221. For example, as shown in FIG. 6, there may be 12 first type of spray nozzles 121 and second type of spray nozzles 221. The second type of spray nozzles 221 form the inner periphery of nozzles in the spray assembly 129. The first type of spray nozzles 121 form the outer periphery of the nozzles in the spray assembly 129.

The first and second types of spray nozzles 121, 221 spray the freezing zone liquid stream 130, 230 with a liquid distribution of 151, 251, respectively, into the middle controlled freeze zone section 108. Each liquid distribution 151, 251 has a central spray axis about which spray is dispersed. The central spray axis is generally coextensive with the axis 112-112 and 212-212, respectively, when the liquid distribution of 151, 251 is symmetrical, but may diverge, e.g., when the liquid distribution 151, 251 is asymmetrical. The freezing zone liquid stream 130, 230 is injected into the controlled freeze zone section 108 at a temperature and pressure at which the solid and the hydrocarbon-enriched vapor stream form.

The freezing zone liquid stream 130, 230 comprises a freezing zone liquid stream outermost portion 131, 231. The freezing zone liquid stream outermost portion 131 of the freezing zone liquid stream 130 sprayed from the first type of spray nozzle 121 may be directly adjacent to the controlled freeze zone wall 46. The freezing zone liquid stream outermost portion 131 may be an outermost boundary of the freezing zone liquid stream 130. In other words, the freezing zone liquid stream outermost portion 131 forms a first part of the outermost perimeter of the freezing zone liquid stream 130 sprayed from the first nozzle 121. And this first part of the outermost perimeter is closer to the controlled freeze zone wall 46 than any other portion of the outermost perimeter.

The freezing zone liquid stream 130, 230 may also comprise a freezing zone liquid stream innermost portion 132, 232. The freezing zone liquid stream innermost portion 132 of the freezing zone liquid stream sprayed 130 sprayed from the first type of spray nozzle 121 is not directly adjacent to the controlled freeze zone wall 46. This freezing zone liquid stream innermost portion 132 is farther from the controlled freeze zone wall 46 than the freezing zone liquid stream outermost portion 131. The freezing zone liquid stream innermost portion 132 may be an innermost boundary of the freezing zone liquid stream 130. In other words, the freezing zone liquid stream innermost portion 132 forms a second part of the outermost perimeter of the freezing zone liquid stream 130 sprayed from the first nozzle 121. And this second part of the outermost perimeter is farther from the controlled freeze zone wall 46 than any other portion of the outermost perimeter.

The characteristics such as, but not limited to spray angle and symmetricity, of the liquid stream 130, 230 from the innermost portion 131, 231 to the outermost portion 132, 232 is defined as the liquid distribution 151, 251.

The freezing zone liquid stream outermost portion 231 and freezing zone liquid stream innermost portion 232 of the freezing zone liquid stream 230 sprayed from the second type of spray nozzle 221 is farther from the controlled freeze zone wall 46 than the freezing zone liquid stream outermost portion 131 of the freezing zone liquid stream 130 sprayed from the first type of spray nozzle 121. The freezing zone liquid stream outermost portion 231 and freezing zone liquid stream innermost portion 232 may or may not be farther from the controlled freeze zone wall 46 than the freezing zone liquid stream innermost portion 132 of the freezing zone liquid stream 130 sprayed from the first type of spray nozzle 121.

The first type of spray nozzle 121 may be directly adjacent to the controlled freeze zone wall 46. Specifically, the first type of spray nozzle 121 may be directly adjacent to the controlled freeze zone internal surface 31 of the controlled freeze zone wall 46. The first type of spray nozzle 121 may be at a periphery of the middle controlled freeze zone section 108. The first type of spray nozzle 121 may be closer to the controlled freeze zone wall 46 than the second type of spray nozzle 221. In other words, the second type of spray nozzle 221 may be farther away from the controlled freeze zone wall 46 than the first type of spray nozzle 121.

The axis of the first type of spray nozzle 121 may be at the first angle 122 to the controlled freeze zone wall 46. The first angle 122 may be defined by a first longitudinal spray nozzle axis 112-112 and a longitudinal controlled freeze zone wall axis 111-111. In other words, the bounds of the first angle 122 may be the first longitudinal spray nozzle axis 112-112 and the longitudinal controlled freeze zone wall axis 111-111. The first angle 122 may be any suitable angle, such as but not limited to, any angle within and including 0 to 60 degrees. For example, the first angle 122 may be 0 degrees, 15 degrees, 30 degrees or 45 degrees.

The first angle 122 of the axis of the first type of spray nozzle 121, 506 may be constructed and arranged to direct the freezing zone liquid stream outermost portion 131 so as to keep the sprayed freezing zone liquid stream away from the controlled freeze zone wall 46, e.g., to reduce, eliminate, and/or minimize spray liquid impingement on the controlled freeze zone wall 46 (i.e., the longitudinal controlled freeze zone wall axis 111-111). In some embodiments, reduction and/or minimization of spray liquid impingement on the controlled freeze zone wall 46 may not eliminate spray liquid impingement on the controlled freeze zone wall 46. The first angle 122 may be constructed and arranged at this position to direct the freezing zone liquid stream away from the controlled freeze zone wall 46. As shown from a top view in FIG. 6, the first angle 122 may lead to an elongated ellipsoid spray projection.

When the innermost portion 131, 231 of the liquid 130 sprayed from the first type of spray head 121 is angled away from the controlled freeze zone wall 46, the liquid sprayed may not appreciably impinge on the controlled freeze zone wall 46, where it could cause possible solid build-up on the controlled freeze zone wall 46. Consequently, solids such as crystalline solids, fluffy snow and/or slurry like solids, are less likely to build-up on the controlled freeze zone wall 46. This is in contrast to conventional spray assemblies within distillation towers where sprayed liquid impinges on the distillation tower wall.

The second type of spray nozzle 221 may be at the second angle 222 to the controlled freeze zone wall 46. The second angle 222 may be defined by a second longitudinal spray nozzle axis 212-212 and a longitudinal controlled freeze zone wall axis 111-111. In other words, the bounds of the second angle 222 may be the second longitudinal spray nozzle axis 212-212 and the longitudinal controlled freeze zone wall axis 111-111. The second angle 222 may be any suitable angle, such as but not limited to, any angle within and including 0 to 60 degrees. For example, the second angle 222 may be 0 degrees, 15 degrees, 30 degrees or 45 degrees.

The second angle 222 may or may not be constructed and arranged to direct the freezing zone liquid stream outermost portion 232 at about a 0 degree angle or a 0 degree angle (i.e., substantially parallel) to the controlled freeze zone wall 46 (i.e., the longitudinal controlled freeze zone wall axis 111-111) with the second type of spray nozzle 221. Often times the second angle 222 does not have to be constructed and arranged to direct the freezing zone liquid stream outermost portion 232 at about a 0 degree angle or a 0 degree angle (i.e., substantially parallel) to the controlled freeze zone wall 46 (i.e., the longitudinal controlled freeze zone wall axis 111-111) with the second type of spray nozzle 221 because the second type of spray nozzle 221 is far enough from the controlled freeze zone wall 46 that the trajectory of the freezing zone liquid stream 230 from the second type of spray nozzle 221 does not easily impinge on the controlled freeze zone wall 46. As shown from a top view in FIG. 6, the second angle 122 spray projection may form a circle.

Those skilled in the art will understand that the liquid distribution 151, 251 of the types of spray nozzles 121, 221 may be adjusted in a symmetric or asymmetric pattern, as necessary, to optimize the spray coverage across the open space of the cross sectional area of the controlled freeze zone section 108 and still limit spray impingement on the controlled freeze zone tower wall. As discussed above, altering the liquid distribution 151, 251 of the types of spray nozzles 121, 221 will change the central spray axis of the spray pattern.

The first type of spray nozzle 121 may comprise a plurality of nozzles 121 and/or the second type of spray nozzle 221 may comprise a plurality of nozzles 221. Each of the first type of spray nozzles 121 may be at the same angle to another one of the first type of spray nozzles. Each of the first type of spray nozzles 121 may be at a different angle to another one of the first type of spray nozzles. Each of the second type of spray nozzles 221 may be at the same angle to another one of the second type of spray nozzles. Each of the second type of spray nozzles 221 may be at a different angle to another one of the second type of spray nozzles.

The spray assembly 129 may include one or more headers 123 (FIGS. 5-6). Each header 123 may receive either a single or a plurality of the first and second type of spray nozzles 121, 221. Each header may be any suitable header and is not limited to the type of header shown in FIG. 6. For example, a header may be a pipe extending from the controlled freeze zone wall 46 such that a longitudinal axis of the header is perpendicular to the longitudinal controlled freeze zone wall axis 111-111 (i.e., the header extends from, for example, the side of the middle controlled freeze zone section). Another example header may enter the controlled freeze zone section from the ellipsoid head at the top of the controlled freeze zone section.

The spray assembly 129 may also include a spray pump 128 (FIGS. 1-4). The spray pump 128 pumps the liquid to the spray nozzles 121, 221. Instead of a spray pump 128, gravity may induce flow in the liquid.

The solid formed in the middle controlled freeze zone section 108, falls toward the melt tray assembly 139. Most, if not all, solids do not fall toward the controlled freeze zone wall 46 because of the above-described arrangement of the spray assembly 120. To address instances where solids still fall toward and adhere to the controlled freeze zone wall 46, the middle controlled freeze zone section 108 may also include at least one of (a) a heating mechanism and (b) a surface treated by a treatment mechanism, such as those described in the applications entitled "Method and Device for Separating Hydrocarbons and Contaminants with a Heating Mechanism to Destabilize and/or Prevent Adhesion of Solids" (U.S. Application No. 61/912,986) and "Method and Device for Separating Hydrocarbons and Contaminants with a Surface Treatment Mechanism," (U.S. Application No. 61/912,987) respectively, each by Jaime Valencia, et al. and filed on the same day as the instant application. Using (a) and (b) may minimize the chance of solid build-up more than using less than all three of these mechanisms.

The solid formed in the middle controlled freeze zone section 108 forms the liquid/slurry mix in the melt tray assembly 139. The liquid/slurry mix flows from the middle controlled freeze zone section 108 to the lower section 106. The liquid/slurry mix flows from the bottom of the middle controlled freeze zone section 108 to the lower section 106 via a line 22 (FIGS. 1-4). The line 22 may be an exterior line. The line 22 may extend from the distillation tower 104, 204. The line 22 may extend from the middle controlled freeze zone section 108. The line may extend from the lower section 106. The line 22 may extend from an outer surface of the distillation tower 104, 204.

The temperature in the middle controlled freeze zone section 108 cools down as the vapor stream travels from the bottom of the middle controlled freeze zone section 108 to the top of the middle controlled freeze zone section 108. The methane in the vapor stream rises from the middle controlled freeze zone section 108 to the upper section 110. Some contaminants may remain in the methane and also rise. The contaminants in the vapor stream tend to condense or solidify with the colder temperatures and fall to the bottom of the middle controlled freeze zone section 108.

The solids form the liquid and/or slurry mix when in the liquid 130. The liquid and/or slurry mix flows from the middle controlled freeze zone section 108 to the lower distillation section 106. The liquid and/or slurry mix flows from the bottom of the middle controlled freeze zone section 108 to the top of the lower section 106 via a line 22 (FIGS. 1-4). The line 22 may be an exterior line. The line 22 may extend from the distillation tower 104, 204. The line 22 may extend from the middle controlled freeze zone section 108. The line may extend to the lower section 106.

The vapor stream that rises in the middle controlled freeze zone section 108 and does not form solids or otherwise fall to the bottom of the middle controlled freeze zone section 108, rises to the upper section 110. The upper section 110 operates at a temperature and pressure and contaminant concentration at which no solid forms. The upper section 110 is constructed and arranged to cool the vapor stream to separate the methane from the contaminants Reflux in the upper section 110 cools the vapor stream. The reflux is introduced into the upper section 110 via line 18. Line 18 may extend to the upper section 110. Line 18 may extend from an outer surface of the distillation tower 104, 204.

After contacting the reflux in the upper section 110, the feed stream forms a vapor stream and a liquid stream. The vapor stream mainly comprises methane. The liquid stream comprises relatively more contaminants. The vapor stream rises in the upper section 110 and the liquid falls to a bottom of the upper section 110.

To facilitate separation of the methane from the contaminants when the stream contacts the reflux, the upper section 110 may include one or more mass transfer devices 176. Each mass transfer device 176 helps separate the methane from the contaminants. Each mass transfer device 176 may comprise any suitable separation device, such as a tray with perforations, a section of random or structured packing, etc., to facilitate contact of the vapor and liquid phases.

After rising, the vapor stream may exit the distillation tower 104, 204 through line 14. The line 14 may emanate from an upper part of the upper section 110. The line 14 may extend from an outer surface of the upper section 110.

From line 14, the vapor stream may enter a condenser 122. The condenser 122 cools the vapor stream to form a cooled stream. The condenser 122 at least partially condenses the stream.

After exiting the condenser 122, the cooled stream may enter a separator 124. The separator 124 separates the vapor stream into liquid and vapor streams. The separator may be any suitable separator that can separate a stream into liquid and vapor streams, such as a reflux drum.

Once separated, the vapor stream may exit the separator 124 as sales product. The sales product may travel through line 16 for subsequent sale to a pipeline and/or condensation to be liquefied natural gas.

Once separated, the liquid stream may return to the upper section 110 through line 18 as the reflux. The reflux may travel to the upper section 110 via any suitable mechanism, such as a reflux pump 150 (FIGS. 1 and 3) or gravity (FIGS. 2 and 4).

The liquid stream (i.e., freezing zone liquid stream) that falls to the bottom of the upper section 110 collects at the bottom of the upper section 110. The liquid may collect on tray 183 (FIGS. 1 and 3) or at the bottommost portion of the upper section 110 (FIGS. 2 and 4). The collected liquid may exit the distillation tower 104, 204 through line 20 (FIGS. 1 and 3) or outlet 260 (FIGS. 2 and 4). The line 20 may emanate from the upper section 110. The line 20 may emanate from a bottom end of the upper section 110. The line 20 may extend from an outer surface of the upper section 110.

The line 20 and/or outlet 260 connect to a line 41. The line 41 leads to the spray assembly 129 in the middle controlled freeze zone section 108. The line 41 emanates from the holding vessel 126. The line 41 may extend to an outer surface of the middle controlled freeze zone section 110.

The line 20 and/or outlet 260 may directly or indirectly (FIGS. 1-4) connect to the line 41. When the line 20 and/or outlet 260 directly connect to the line 41, the liquid spray may be pumped to the spray nozzle(s) 120 via any suitable mechanism, such as the spray pump 128 or gravity. When the line 20 and/or outlet 260 indirectly connect to the line 41, the lines 20, 41 and/or outlet 260 and line 41 may directly connect to a holding vessel 126 (FIGS. 1 and 3). The holding vessel 126 may house at least some of the liquid before it is sprayed by the nozzle(s). The liquid may be pumped from the holding vessel 126 to the spray nozzle(s) 120 via any suitable mechanism, such as the spray pump 128 (FIGS. 1-4) or gravity. The holding vessel 126 may be needed when there is not a sufficient amount of liquid stream at the bottom of the upper section 110 to feed the spray nozzles 120.

The method may include maintaining an upper section 110. The upper section 110 operates as previously discussed. The method may also include separating the feed stream in the upper section 110 as previously discussed.

It is important to note that the steps depicted in FIG. 7 are provided for illustrative purposes only and a particular step may not be required to perform the inventive methodology. Moreover, FIG. 7 may not illustrate all the steps that may be performed. The claims, and only the claims, define the inventive system and methodology.

Disclosed aspects may be used in hydrocarbon management activities. As used herein, "hydrocarbon management" or "managing hydrocarbons" includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities. The term "hydrocarbon management" is also used for the injection or storage of hydrocarbons or $CO_2$, for example the sequestration of $CO_2$, such as reservoir evaluation, development planning, and reservoir management. The disclosed methodologies and techniques may be used in extracting hydrocarbons from a subsurface region and processing the hydrocarbons. Hydrocarbons and contaminants may be extracted from a reservoir and processed. The hydrocarbons and contaminants may be processed, for example, in the distillation tower previously described. After the hydrocarbons and contaminants are processed, the hydrocarbons may be extracted from the processor, such as the distillation tower, and produced. The contaminants may be discharged into the Earth, etc. For example, as shown in FIG. 7, the method for producing hydrocarbons may include producing 509 the hydrocarbon-enriched vapor stream extracted from the distillation tower. The method may also include removing the hydrocarbon-enriched vapor stream from the distillation tower before producing 509 the hydrocarbon-enriched vapor stream. The initial hydrocarbon extraction from the reservoir may be accomplished by drilling a well using hydrocarbon drilling equipment. The equipment and techniques used to drill a well and/or extract these hydrocarbons are well known by those skilled in the relevant art. Other hydrocarbon extraction activities and, more generally, other hydrocarbon management activities, may be performed according to known principles.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numeral ranges provided. Accordingly, these terms should be interpreted as indicating that insubstantial or inconsequential modifications or alterations of the subject matter described are considered to be within the scope of the disclosure.

It should be understood that the numerous changes, modifications, and alternatives to the preceding disclosure can be made without departing from the scope of the disclosure. The preceding description, therefore, is not meant to limit the scope of the disclosure. Rather, the scope of the disclosure is to be determined only by the appended claims and their equivalents. It is also contemplated that structures and features in the present examples can be altered, rearranged, substituted, deleted, duplicated, combined, or added to each other.

The articles "the," "a" and "an" are not necessarily limited to mean only one, but rather are inclusive and open ended so as to include, optionally, multiple such elements.

What is claimed is:

1. A method for producing hydrocarbons comprising:
   maintaining a controlled freeze zone section in a distillation tower that receives a freezing zone liquid stream to form a solid and a hydrocarbon-enriched vapor stream in the controlled freeze zone section;
   maintaining a spray assembly in the controlled freeze zone section, wherein the spray assembly comprises a first type of spray nozzle on an outer periphery of the spray nozzle assembly and a second type of spray nozzle interior to the first type of spray nozzle in the spray assembly, wherein the first type of spray nozzle orients spray at a first angle with respect to a controlled freeze zone wall and the second type of spray nozzle orients spray at a second angle with respect to the controlled freeze zone wall, wherein the first angle and the second angle are different, and wherein the first angle is configured such that the spray liquid does not impinge on the controlled freeze zone wall;
   injecting the freezing zone liquid stream into the controlled freeze zone section through the spray assembly at a temperature and pressure at which the solid and the hydrocarbon-enriched vapor stream form; and
   extracting the hydrocarbon-enriched vapor stream from the distillation tower.

2. The method of claim 1, wherein injecting the freezing zone liquid stream into the controlled freeze zone section through the spray assembly comprises flowing the freezing zone liquid stream through a side of the controlled freeze zone section.

3. The method of claim 1, wherein injecting the freezing zone liquid stream into the controlled freeze zone section through the spray assembly comprises flowing the freezing zone liquid stream through a top of the controlled freeze zone section.

4. The method of claim 1, wherein the first angle is configured by angling at least one of the first type of spray nozzles towards the interior of the tower and varying the distribution of the spray liquid coming out of at least one of the first type of spray nozzles in a pattern to keep the sprayed freezing zone liquid stream away from the controlled freeze zone wall.

5. The method of claim 1, wherein the first angle may be defined by a longitudinal spray nozzle axis and a longitudinal controlled freeze zone wall axis and wherein the first angle is from 0 to 60 degrees.

6. The method of claim 1, wherein the first angle creates an elongated ellipsoid spray projection.

7. The method of claim 1, wherein the second angle may be defined by a longitudinal spray nozzle axis and a longitudinal controlled freeze zone wall axis and wherein the second angle is from 0 to 60 degrees.

* * * * *